(12) United States Patent
Maccree

(10) Patent No.: US 8,882,805 B1
(45) Date of Patent: Nov. 11, 2014

(54) SPINAL FIXATION SYSTEM

(76) Inventor: Lawrence Maccree, Knoxville, TN (US)

( * ) Notice: Subject to any disclaimer, the term of this patent is extended or adjusted under 35 U.S.C. 154(b) by 0 days.

(21) Appl. No.: 13/565,742

(22) Filed: Aug. 2, 2012

Related U.S. Application Data

(60) Provisional application No. 61/514,442, filed on Aug. 2, 2011.

(51) Int. Cl.
*A61B 17/70* (2006.01)
*A61F 2/30* (2006.01)

(52) U.S. Cl.
CPC ..... *A61B 17/7067* (2013.01); *A61F 2002/3055* (2013.01)
USPC .......................................................... 606/249

(58) Field of Classification Search
CPC ........... A61B 17/7067; A61B 17/7049; A61B 17/705; A61B 17/7064; A61B 17/842; A61B 17/80; A61B 17/86; A61F 2/4405; A61F 2002/30242; A61F 2002/30481; A61F 2002/30512; A61F 2002/30523; A61F 2002/3055; A61F 2002/30649; A61F 2002/30507
USPC .................. 606/248, 249, 279, 280, 247, 246
See application file for complete search history.

(56) References Cited

U.S. PATENT DOCUMENTS

| | | | |
|---|---|---|---|
| 267,269 A | 11/1882 | Smith et al. | |
| 2,677,369 A | 5/1954 | Knowles | |
| 3,025,853 A | 3/1962 | Mason | |
| 3,242,922 A | 3/1966 | Thomas | |
| 3,426,364 A | 2/1969 | Lumb | |
| 3,648,691 A | 3/1972 | Lumb et al. | |
| 3,805,219 A | 4/1974 | Bright | |
| 4,143,883 A | 3/1979 | Paynter | |
| 4,448,191 A | 5/1984 | Rodnyansky et al. | |
| 4,554,914 A | 11/1985 | Kapp et al. | |
| 4,570,618 A | 2/1986 | Wu | |
| 4,604,995 A | 8/1986 | Stephens et al. | |
| 4,643,178 A | 2/1987 | Nastari et al. | |
| 4,655,462 A | 4/1987 | Balsells | |
| 4,773,402 A | 9/1988 | Asher et al. | |
| 4,913,134 A | 4/1990 | Luque | |
| 5,011,484 A * | 4/1991 | Breard | 606/249 |
| 5,084,049 A | 1/1992 | Asher et al. | |
| 5,092,866 A | 3/1992 | Breard et al. | |
| 5,167,662 A | 12/1992 | Hayes et al. | |
| 5,180,393 A | 1/1993 | Commarmond | |
| 5,261,914 A | 11/1993 | Warren | |
| 5,304,178 A | 4/1994 | Stahurski | |
| 5,352,225 A | 10/1994 | Yuan et al. | |

(Continued)

FOREIGN PATENT DOCUMENTS

| | | |
|---|---|---|
| DE | 3114872 | 10/1982 |
| EP | 1872731 | 1/2008 |

(Continued)

*Primary Examiner* — Pedro Philogene
(74) *Attorney, Agent, or Firm* — Jonathan Spangler; Jennifer Russell

(57) ABSTRACT

A spinal fixation device including two plates, a connector element for either coupling the plates in a fixed manner between the L5 vertebrae and the sacrum, and an anchor element to anchor the spinal fixation device to the sacrum. Each plate is preferably equipped with integral spikes on the inwardly facing surfaces for pressing into the spinal processes and thereby augmenting the purchase between the plates and the spinous processes. Each plate contains a central aperture through which the connector element passes in order to couple the plates together.

11 Claims, 3 Drawing Sheets

(56) References Cited

U.S. PATENT DOCUMENTS

| | | | |
|---|---|---|---|
| 5,470,333 A | 11/1995 | Ray | |
| 5,496,318 A | 3/1996 | Howland et al. | |
| 5,531,747 A | 7/1996 | Ray | |
| 5,609,634 A | 3/1997 | Voydeville | |
| 5,645,599 A | 7/1997 | Samani | |
| 5,722,976 A | 3/1998 | Brown | |
| 5,836,948 A | 11/1998 | Zucherman et al. | |
| 6,048,342 A | 4/2000 | Zucherman et al. | |
| 6,312,431 B1 * | 11/2001 | Asfora | 606/279 |
| 6,364,883 B1 | 4/2002 | Santilli | |
| 6,582,433 B2 | 6/2003 | Yun | |
| 6,626,944 B1 | 9/2003 | Taylor | |
| 6,641,585 B2 | 11/2003 | Sato et al. | |
| 6,652,527 B2 | 11/2003 | Zucherman et al. | |
| 6,652,534 B2 | 11/2003 | Zucherman et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,712,819 B2 | 3/2004 | Zucherman et al. | |
| 6,761,720 B1 | 7/2004 | Senegas | |
| 6,796,983 B1 | 9/2004 | Zucherman et al. | |
| 7,048,736 B2 | 5/2006 | Robinson et al. | |
| 7,201,775 B2 | 4/2007 | Gorensek et al. | |
| 7,252,673 B2 | 8/2007 | Lim | |
| 7,306,628 B2 | 12/2007 | Zucherman et al. | |
| 7,361,179 B2 | 4/2008 | Rousseau et al. | |
| 7,520,888 B2 | 4/2009 | Trieu | |
| 7,588,592 B2 | 9/2009 | Winslow et al. | |
| 7,727,233 B2 | 6/2010 | Blackwell et al. | |
| 7,758,274 B2 | 7/2010 | Paul | |
| 7,776,069 B2 | 8/2010 | Taylor | |
| 7,828,847 B2 | 11/2010 | Abdou | |
| 7,837,688 B2 | 11/2010 | Boyer, II et al. | |
| 7,842,074 B2 | 11/2010 | Abdou | |
| 8,048,120 B1 | 11/2011 | Fallin et al. | |
| 8,128,659 B2 | 3/2012 | Ginsberg et al. | |
| 8,206,420 B2 * | 6/2012 | Patel et al. | 606/249 |
| 8,241,330 B2 | 8/2012 | Lamborne et al. | |
| 8,262,697 B2 | 9/2012 | Kirschman | |
| 8,343,190 B1 | 1/2013 | Mueller et al. | |
| 8,382,801 B2 | 2/2013 | Lamborne et al. | |
| 8,430,911 B2 * | 4/2013 | Chin et al. | 606/248 |
| 8,496,689 B2 * | 7/2013 | Massoudi | 606/249 |
| 2001/0021850 A1 | 9/2001 | Zucherman et al. | |
| 2003/0040746 A1 | 2/2003 | Mitchell et al. | |
| 2003/0065330 A1 | 4/2003 | Zucherman et al. | |
| 2003/0094812 A1 | 5/2003 | Balsells | |
| 2003/0216736 A1 | 11/2003 | Robinson et al. | |
| 2003/0236472 A1 | 12/2003 | Van Hoeck et al. | |
| 2004/0260291 A1 | 12/2004 | Jensen | |
| 2005/0033434 A1 | 2/2005 | Berry | |
| 2005/0165398 A1 | 7/2005 | Reiley | |
| 2005/0203512 A1 | 9/2005 | Hawkins et al. | |
| 2005/0203624 A1 | 9/2005 | Serhan et al. | |
| 2006/0036256 A1 | 2/2006 | Carl et al. | |
| 2006/0036258 A1 | 2/2006 | Zucherman et al. | |
| 2006/0064095 A1 | 3/2006 | Senn et al. | |
| 2006/0106381 A1 | 5/2006 | Ferree et al. | |
| 2006/0106397 A1 | 5/2006 | Lins | |
| 2006/0136060 A1 | 6/2006 | Taylor | |
| 2006/0235532 A1 | 10/2006 | Meunier et al. | |
| 2006/0241601 A1 | 10/2006 | Trautwein et al. | |
| 2006/0247633 A1 | 11/2006 | Winslow et al. | |
| 2006/0247640 A1 | 11/2006 | Blackwell et al. | |
| 2006/0293662 A1 | 12/2006 | Boyer, II et al. | |
| 2007/0093823 A1 | 4/2007 | Booth et al. | |
| 2007/0093825 A1 | 4/2007 | Ferree et al. | |
| 2007/0093828 A1 | 4/2007 | Abdou | |
| 2007/0100340 A1 | 5/2007 | Lange et al. | |
| 2007/0173832 A1 | 7/2007 | Tebbe et al. | |
| 2007/0225724 A1 | 9/2007 | Edmond | |
| 2007/0233074 A1 | 10/2007 | Anderson et al. | |
| 2007/0233077 A1 | 10/2007 | Khalili | |
| 2007/0233088 A1 | 10/2007 | Edmond | |
| 2007/0233096 A1 | 10/2007 | Garcia-Bengochea | |
| 2007/0233129 A1 | 10/2007 | Bertagnoli et al. | |
| 2007/0270812 A1 | 11/2007 | Peckham | |
| 2007/0270824 A1 | 11/2007 | Lim et al. | |
| 2007/0270827 A1 | 11/2007 | Lim et al. | |
| 2007/0270874 A1 | 11/2007 | Anderson | |
| 2007/0276370 A1 | 11/2007 | Altarac et al. | |
| 2007/0299445 A1 | 12/2007 | Shadduck et al. | |
| 2008/0027438 A1 | 1/2008 | Abdou | |
| 2008/0033552 A1 | 2/2008 | Lee et al. | |
| 2008/0039837 A1 | 2/2008 | Gambale | |
| 2008/0051896 A1 | 2/2008 | Suddaby | |
| 2008/0114401 A1 | 5/2008 | Liu et al. | |
| 2008/0114455 A1 | 5/2008 | Lange et al. | |
| 2008/0140125 A1 | 6/2008 | Mitchell et al. | |
| 2008/0161818 A1 | 7/2008 | Kloss et al. | |
| 2008/0167655 A1 | 7/2008 | Wang et al. | |
| 2008/0177271 A1 | 7/2008 | Yeh | |
| 2008/0177298 A1 | 7/2008 | Zucherman et al. | |
| 2008/0177391 A1 | 7/2008 | Mitchell et al. | |
| 2008/0234735 A1 | 9/2008 | Joshi | |
| 2008/0269904 A1 | 10/2008 | Voorhies | |
| 2008/0281359 A1 | 11/2008 | Abdou | |
| 2008/0294199 A1 | 11/2008 | Kohm et al. | |
| 2008/0300686 A1 | 12/2008 | Khoo | |
| 2008/0312741 A1 | 12/2008 | Lee et al. | |
| 2009/0054931 A1 | 2/2009 | Metz-Stavenhagen | |
| 2009/0062915 A1 | 3/2009 | Kohm et al. | |
| 2009/0062918 A1 | 3/2009 | Wang et al. | |
| 2009/0082808 A1 | 3/2009 | Butler et al. | |
| 2009/0105773 A1 | 4/2009 | Lange et al. | |
| 2009/0198277 A1 | 8/2009 | Gordon et al. | |
| 2009/0204151 A1 | 8/2009 | Bracken | |
| 2009/0264927 A1 | 10/2009 | Ginsberg et al. | |
| 2009/0326581 A1 | 12/2009 | Galley et al. | |
| 2010/0069965 A1 | 3/2010 | Abdou | |
| 2010/0087860 A1 | 4/2010 | Chin et al. | |
| 2010/0087869 A1 | 4/2010 | Abdou | |
| 2010/0211101 A1 | 8/2010 | Blackwell et al. | |
| 2010/0211102 A1 | 8/2010 | Belliard et al. | |
| 2010/0318128 A1 | 12/2010 | Abdou | |
| 2011/0004248 A1 | 1/2011 | Abdou | |
| 2011/0022090 A1 | 1/2011 | Gordon et al. | |
| 2011/0054531 A1 | 3/2011 | Lamborne et al. | |
| 2011/0066186 A1 | 3/2011 | Boyer, II et al. | |
| 2011/0144692 A1 | 6/2011 | Saladin et al. | |
| 2011/0319936 A1 | 12/2011 | Gordon et al. | |
| 2012/0016418 A1 | 1/2012 | Chin et al. | |
| 2012/0016419 A1 | 1/2012 | Aflatoon | |
| 2012/0065682 A1 | 3/2012 | Duong et al. | |
| 2012/0089184 A1 | 4/2012 | Yeh | |
| 2012/0101528 A1 | 4/2012 | Souza et al. | |
| 2012/0109198 A1 | 5/2012 | Dryer et al. | |
| 2012/0109203 A1 | 5/2012 | Dryer et al. | |
| 2012/0109205 A1 | 5/2012 | Mitchell et al. | |
| 2012/0136390 A1 | 5/2012 | Butler et al. | |
| 2012/0150228 A1 | 6/2012 | Zappacosta et al. | |
| 2012/0191135 A1 | 7/2012 | Abdou | |
| 2012/0215261 A1 | 8/2012 | Massoudi | |
| 2012/0221050 A1 | 8/2012 | Ingalhalikar et al. | |
| 2012/0226314 A1 | 9/2012 | Chin et al. | |
| 2012/0245641 A1 | 9/2012 | Mekhail et al. | |
| 2012/0259364 A1 * | 10/2012 | Lange | 606/246 |
| 2012/0290008 A1 | 11/2012 | Kirschman | |
| 2012/0310282 A1 | 12/2012 | Abdou | |
| 2013/0012996 A1 | 1/2013 | Samani et al. | |
| 2013/0030467 A1 | 1/2013 | Karas et al. | |
| 2013/0060284 A1 | 3/2013 | Abdou | |
| 2013/0072979 A1 | 3/2013 | Butler et al. | |
| 2013/0103086 A1 | 4/2013 | Marik et al. | |
| 2013/0158604 A1 | 6/2013 | Okamoto | |
| 2013/0184751 A1 | 7/2013 | Siegfried | |
| 2013/0184752 A1 | 7/2013 | Binder | |
| 2013/0184754 A1 | 7/2013 | Taber et al. | |
| 2013/0190820 A1 | 7/2013 | Siegfried et al. | |
| 2013/0197581 A1 | 8/2013 | Justis et al. | |
| 2013/0204301 A1 | 8/2013 | Mitchell et al. | |

(56) References Cited

U.S. PATENT DOCUMENTS

FOREIGN PATENT DOCUMENTS

| | | |
|---|---|---|
| FR | 1037262 | 9/1953 |
| FR | 2703239 | 10/1994 |
| FR | 2806614 | 9/2001 |
| FR | 2902639 | 12/2007 |
| FR | 2930718 | 11/2009 |
| GB | 780652 | 8/1957 |
| WO | WO 93/14721 | 8/1993 |
| WO | WO 94/20048 | 9/1994 |
| WO | WO 03/007829 | 1/2003 |
| WO | WO 03/024298 | 3/2003 |
| WO | WO 2004/039283 | 5/2004 |
| WO | WO 2006/086241 | 8/2006 |
| WO | WO 2006/110578 | 10/2006 |
| WO | WO 2007/038475 | 4/2007 |
| WO | WO 2007/087535 | 8/2007 |
| WO | WO 2007/089975 | 8/2007 |
| WO | WO 2007/106573 | 9/2007 |
| WO | WO 2008/067452 | 6/2008 |
| WO | WO 2008/106140 | 9/2008 |
| WO | WO 2009/135208 | 11/2009 |
| WO | WO 2009/152126 | 12/2009 |

\* cited by examiner

SPINAL FIXATION SYSTEM

CROSS REFERENCE TO RELATED APPLICATIONS

This application claims the benefit of the filing date of U.S. Provisional Application No. 61/514,442, which was filed on Aug. 2, 2011. The contents of U.S. Application No. 61/514,442 are incorporated by reference as part of this application.

BACKGROUND OF THE INVENTION

I. Field of the Invention

The present invention relates generally to spinal surgery, and more particularly to devices for fusing adjacent spinous processes to stabilize the vertebral segment associated with the particular spinous processes or with a spinous process and an adjacent vertebrae or sacrum.

II. Discussion of the Prior Art

The human spinal column is made up of two basic components, vertebrae (bone) and intervertebral discs (gel-like cushions that absorb pressure and prevent vertebrae from rubbing together). Vertebrae and intervertebral discs stack together to form a column that provides support and structure for the body while still allowing a large degree of motion and flexibility. The spinal column also serves to protect the spinal cord (a bundle of nerves linking the brain to the rest of the body) that runs through an opening formed in the center of the column. Two nerve roots exit the spinal column at each level through spaces formed between the vertebrae. Various traumatic events and degenerative conditions may result in undesirable motion or changes in disc height, both of which may cause chronic pain for the affected individual. The pain is generally caused when changes in disc height and improper motion allow adjacent vertebrae to impinge upon exiting nerve roots. The degree and treatment of pain varies by individual but in many instances the pain can be disabling and uncontrollable by non-invasive means, leaving surgery as the only viable option. Often in such a case, two or more vertebrae are fused together, employing various instrumentation and methods to correct disc height and prevent improper movement of the vertebrae while fusion occurs, thereby eliminating or at least reducing the pain of the affected individual.

While there are a variety of systems and methods for effecting spinal fixation while fusion occurs, one of the more common methods involves securing pedicle screws into the pedicles of the two or more adjacent vertebrae to be fixed. The challenge in this method is securing the pedicle screws without breaching, cracking, or otherwise compromising the pedicle wall, which may occur if the screw is not properly aligned with the pedicle axis. If the pedicle (or more specifically, the cortex of the medial wall, lateral wall, superior wall and/or inferior wall) is breached, cracked, or otherwise compromised, the patient may experience pain or neurological deficit due to unwanted contact between the pedicle screw and delicate neural structures, such as the spinal cord or exiting nerve roots. This may necessitate revision surgery, which is disadvantageously painful for the patient and costly, both in terms of recovery time and hospitalization.

Alternative systems and methods include attaching two spinous processes by way of a device. The challenge in this method is securing the device to two or more spinous processes when one spinous process is damaged or broken. Another challenge is securing the device to the sacrum which has an extremely small, if any, spinous process.

The present invention is directed to overcome one or more shortcomings encountered with current fixation devices and systems.

SUMMARY OF THE INVENTION

The present invention relates to a spinal fixation device designed to be attached to spinous processes of neighboring vertebrae, or to a spinous process at one end and to the sacrum at the other end, of the spine for immobilizing the vertebrae in order to promote fusion therebetween. The spinal fixation device may be used alone (that is, without any supplemental fusion devices, such as interbody fusion implants) or with supplemental fixation devices. In either event, the spinal fixation device allows fusion to occur between the adjacent spinous processes by maintaining them in an immobilized, locked relationship such that a boney bridge can form therebetween. The formation of the fusion bridge between the adjacent spinous processes may be augmented or facilitated by placing fusion-enhancing compounds between the spinous processes, including but not limited to allograft bone, autograft bone, bone morphogenic protein (BMP), calcium hydroxyapatite, demineralized bone matrix, collagen bone graft matrix (e.g. Formagraft®), and stem cell material (e.g. Osteocel®) and/or any number of suitable biomaterials.

According to one embodiment of the present invention, the spinal fixation device includes two plates, a connector element for coupling the plates in a fixed manner about adjacent spinous processes of the spine and an anchor element for anchoring the spinal fixation device to a vertebra or the sacrum. Each plate is preferably equipped with integral spikes on the inwardly facing surfaces for pressing into the spinal processes and thereby augmenting the purchase between the spinous processes and the plates. Each plate contains a central aperture through which the connector element passes in order to couple the plates together. Each plate also contains a fin for coupling the plates to the adjacent vertebrae.

The connector element may be any number of devices capable of coupling the first plate to the second plate. In one embodiment, the connector element may be an elongated bolt member having external ridges (as opposed to threads) to engage corresponding features in the aperture of one plate to prevent any backward motion once received through the aperture. This embodiment is advantageous in that the plates can be easily locked together and tightened by simply pushing the connector element through one plate (with the head received within a corresponding region or recess of the first plate) and into the next (with the ridges locking at each point as the ridged section is advanced through the aperture of the second plate, the head may or may not be fully contained within the first plate). In either embodiment, the head may be constructed like a screw head with an internally disposed recess for receiving a driving element (e.g. hexalobe drive, Phillips screw driver, hex driver, etc. . . . ) or may be constructed without such an internally disposed recess and may instead be driven by an exteriorly placed driving element (e.g. wrench).

The apertures may be provided in any number of different manners to help facilitate coupling the fixation element to the plates. For example, the aperture of one plate may be equipped with any number of suitable features, such as inwardly facing teeth or ridges that engage with the ridges of the connector element. Moreover, the aperture may include a recess therein configured to house a locking element in the form of a canted coil ring member. The coiled ring member is configured to allow uni-directional movement while in a compressed state and bi-directional movement of the connector element while in a relaxed state. The fin on each plate may be any number of shapes to provide additional stability between adjacent spinous processes. The fins may allow for purchase between adjacent vertebrae where the spinal process is damaged or broken or for purchase between the L5 spinous process and the S1 sacrum. The fins may possess any number of elements including spikes or screws in order to attach the fins to the vertebrae.

Any number of suitable instruments may be provided to help facilitate the surgery, including but not limited to instruments for compressing and/or distracting the adjacent spinous processes prior to securing the plates (and thus immobilizing the spinous processes), as well as instruments to facilitate coupling the plates together such as drivers for tightening the connector element to the plates or instruments for compressing the plates together. In one embodiment, the driving or compressing instrument may be equipped with a torque limiting mechanism that produces an audible (e.g. "click") and/or and a tactile alert that lets the surgeon know he or she has applied optimal torque to the fixation element to fix the plates together.

DESCRIPTION OF THE PREFERRED EMBODIMENT

Figure 1:
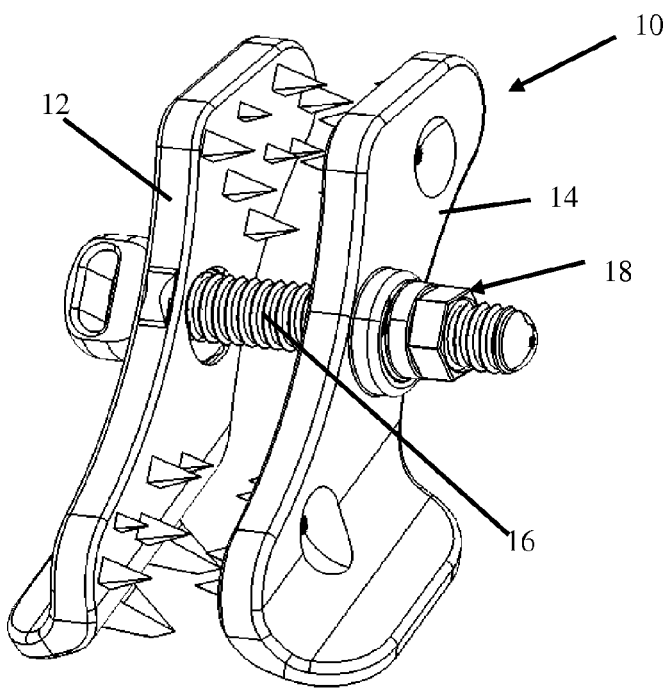
FIG. 1 is a plan view of a spinous process fixation system.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinous process plate system for spinal fusion disclosed herein boasts a variety of inventive features and components that warrant patent protection, both individually and in combination The specifics of the spinous process fixation system 10 will now be described with reference to FIGS. 1-7. The spinous process fixation system 10 includes a first plate 12, a second plate 14, a connector element 16, a locking assembly 18 and an anchor element 160. By way of example, the locking assembly 18 is configured to be assembled with the second plate 14 and provides secure coupling of the coupling member, which in turn maintains the first and second plates 12, 14 in a desired orientation relative to one another. However, it will be appreciated that a variety of locking assemblies for connecting the connector element 16 to the first and second plates 12, 14 known in the art may be used with the spinous process fixation system described herein.

Figure 2:
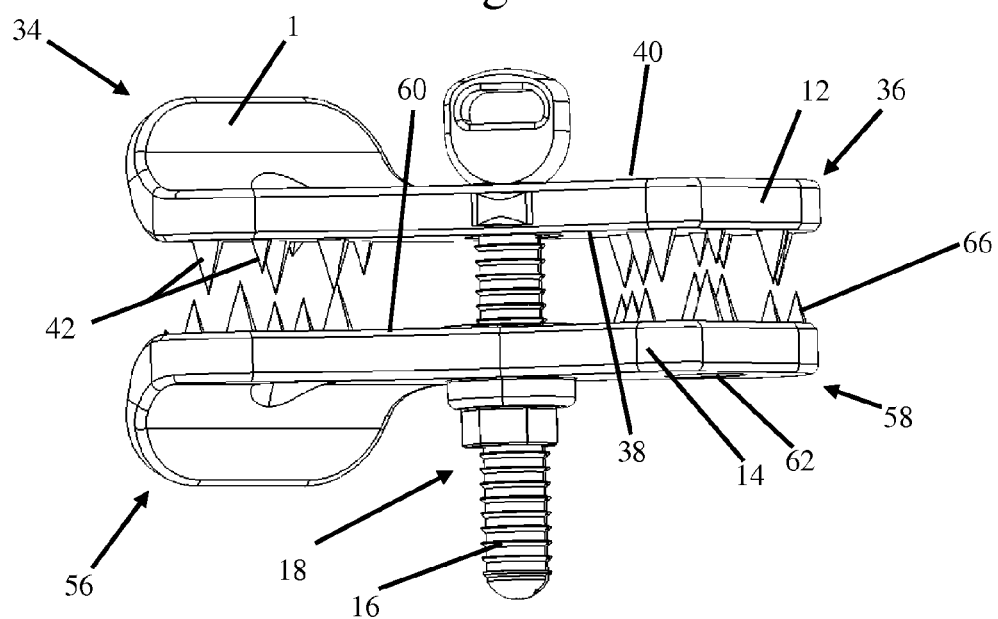
FIG. 2 is a top view of the spinous process fixation system of FIG. 1.

FIGS. 1-2 illustrate an exemplary embodiment of a spinous process fixation system 10 dimensioned for achieving fixation between the L5 spinous process and the sacrum of a spine. The spinous process fixation system 10 includes a first plate 12, a second plate 14, a connector element 16, and a locking assembly 18. Each of the first plate 12 and second plate 14 includes a fin 1, 2. The spinous process fixation system 10 is designed to be attached to a spinous process (e.g. at L5) and the sacrum of the spine for immobilizing the spinous process and sacrum to promote fusion therebetween. The system 10 may be used alone (that is, without any supplemental fusion devices, such as interbody fusion implants) as shown in FIGS. 1-2. Alternatively, the system 10 may be used with supplemental devices, for example such as a fusion implant. In any event, the system 10 allows fusion to occur between the adjacent vertebrae by maintaining them in an immobilized, locked relationship such that a boney bridge can form therebetween. The formation of the fusion bridge between the adjacent vertebrae may be augmented or facilitated by placing fusion-enhancing compounds between the spinous processes (such as, e.g. between the plates 12, 14 or within a fusion implant or other supplemental device), including but not limited to allograft bone, autograft bone, bone morphogenic protein (BMP), calcium hydroxyapatite, demineralized bone matrix, collagen bone graft matrix (e.g. Formagraft®), and stem cell material (e.g. Osteocel®) and/or any number of suitable biomaterials.

Figure 3:
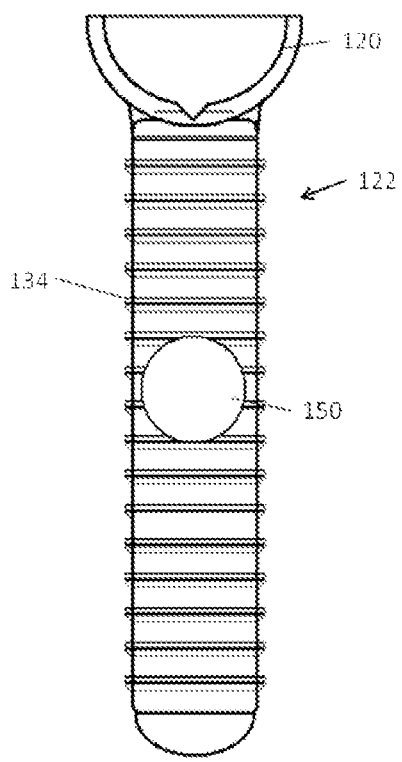
FIG. 3 is a side view of an alternative embodiment of the connector element of the spinous process fixation system of FIG. 1.

An exemplary embodiment of the first plate will now be described with specific reference to FIGS. 3-4. The first plate 12 includes a central body portion extending between a pair of end portions 34, 36. The first plate 12 further includes a first surface 38 dimensioned to face medially, or toward the second plate 14 when assembled and a second surface 40 dimensioned to face laterally, or away from the second plate 14 when assembled. The first plate 12 may be augmented through the use of a plurality spike elements 42, disposed on the first surface 38 of the first plate 12, at the end portions 34, 36. These spike elements 42 are designed to become embedded in the lateral surface of the spinous process when the spinous process fixation system 10 is compressed in place. The first plate also includes fin 1 which integrally extends laterally from end 34 and presents a face that transects the first surface 38 such that the face of fin 1 may rest flush against the sacrum, increasing stability for the plate 12. The fin 1 may contain one or more spikes of any number of suitable sizes.

The first plate 12 may be constructed from any of a variety to suitable materials without departing from the scope of the invention, including but not limited to titanium, polymeric materials (e.g. plastics such as poly-ether-ether-ketone) carbon fiber, and/or any other biologically acceptable material. The first plate 12 may also be provided with any number of suitable dimensions without departing from the scope of the invention. For example, according to one embodiment, the width of the central body portion may range from 5 mm to 20 mm, the width of the end portions 34, 36 may range from 7.5 mm to 25 mm, the length of the central body portion 32 may range from 1 mm to 65 mm, the length of the end portions 34, 36 may range from 7.5 mm to 25 mm, and the thickness of the first plate 12 may range from 1.5 mm to 15 mm. It will be appreciated, however, that these dimensions are provided as examples of those that may be employed with the spinous process fixation system 10 of the present invention and any number of suitable modifications may be made depending upon a variety of factors without departing from the scope of the invention.

The second plate 14 includes similar general features as the first plate 12. The second plate 14 includes a central body portion extending between end portions 56, 58. The second plate 14 further includes a first surface 60 dimensioned to face medially, or toward the first plate 12 when assembled and a second surface 62 dimensioned to face laterally, or away from the first plate 12 when assembled. The second plate 14 may be augmented through the use of a plurality spike elements 66, disposed on the first surface 60 of the second plate 14, at the end portions 56, 58. These spike elements 66 are designed to become embedded in the lateral surface of the spinous process when the spinous process fixation system 10 is compressed in place.

The second plate 14 may be constructed from any of a variety to suitable materials without departing from the scope of the invention, including but not limited to titanium, polymeric materials (e.g. plastics) carbon fiber, and/or any other biologically acceptable material. The second plate 14 may also be provided having any number of suitable dimensions without departing from the scope of the invention. For example, according to one embodiment, the width of the central body portion may range from 5 mm to 20 mm, the width of the end portions 56, 58 may range from 7.5 mm to 25 mm, the length of the central body portion may range from 1 mm to 65 mm, the length of the end portions 56, 58 may range from 7.5 mm to 25 mm, and the thickness of the second plate 14 may range from 1.5 mm to 15 mm. It will be appreciated, however, that these dimensions are provided as examples of those that may be employed with the spinous process fixation system 10 of the present invention and any number of suitable modifications may be made depending upon a variety of factors without departing from the scope of the invention.

The connector element 16 may be constructed from any of a variety of suitable materials without departing from the scope of the invention, including but not limited to titanium, polymeric materials (e.g. plastics) carbon fiber, and/or any other biologically acceptable material. The connector element 16 may also be provided having any number of suitable dimensions without departing from the scope of the invention. For example, according to one embodiment, the width of the connector element 16 may range from 3 mm to 10 mm, the length of the connector element 16 may range from 15 mm to 50 mm, and the ridged portion 124 may range from 5 mm to 47 mm. It will be appreciated, however, that these dimensions are provided as examples of those that may be employed with the spinous process fixation system 10 of the present invention and any number of suitable modifications may be made depending upon a variety of factors without departing from the scope of the invention.

The connector element 16 may be modified in order to receive an anchor element 160 to fix the spinous process fixation system 10 to the sacrum. By way of example only, the connector element 16 may have an anchor aperture 150 through the transverse axis of the shaft 122 (best seen in FIG. 3). The coupling aperture 150 will allow the placement of an anchor element, e.g. a screw (not shown) to be inserted through the shaft 122 of the connector element 16. Upon insertion through the shaft 122 of the connector element 15, the screw can be inserted directly into the sacrum. This configuration will provide additional stabilization and ensure the spinous process fixture system 10 remains in place. The size of the coupling aperture 150 can vary with the size of connector element 16 but may range from a radius of 1 mm to 4 mm. It will be appreciated, however, that these dimensions are provided as examples of those that may be employed with the spinous process fixation system 10 of the present invention and any number of suitable modifications may be made depending upon a variety of factors without departing from the scope of the invention.

Figure 4:
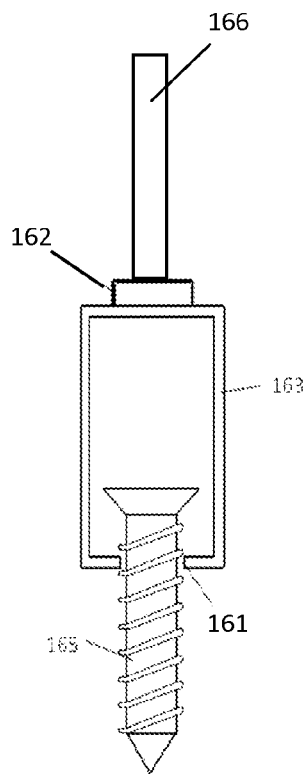
FIGS. 4-5 are front and side views of the anchor element used in conjunction with the spinous process fixation system of FIG. 1.
Figure 5:
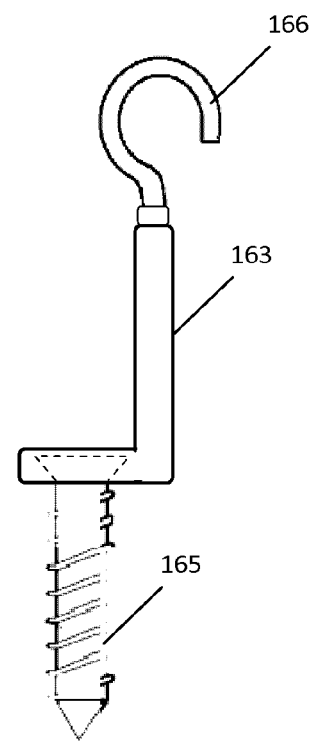

Another exemplary embodiment of an anchor element 160 for providing fixation between the spinous process fixation system 10 and the sacrum is shown in FIGS. 4-5. The anchor element 160 described herein may be used with any spinous process fixation device 10 dimensioned for use at the L5-S1 level of the spine and having a connector element 16 as shown by way of example in FIGS. 1-2. The anchor element 160 includes a body 163 having a screw aperture 161, a rotational device 162, a sacrum screw 165, and coupling hook 166. The body 163 has at least one open side parallel to the sacrum screw 165. The sacrum screw 165 will be inserted into the screw aperture 161 and then into the sacrum. According to this embodiment, the coupling hook 166 is specifically sized and designed to fit snuggly on the connector element 16 of the spinous process fixation system 10. The rotational device 162 is attached to both the body 163 and the coupling hook 166. The coupling hook 166, with the ability to rotate freely, can be placed over the connector element 16 of the spinous process fixation device 10 before the insertion of the sacrum screw 165 into the sacrum. Upon advancing the sacrum screw 165 through the screw aperture 161 and into the sacrum, the coupling hook 166 of the anchor element 160 will firmly grasp the connector element 16 of the spinous process fixation system 10, securing the spinous process fixation system 10 in place and to the sacrum by fixing the distance between the connector element 16 and the sacrum.

Figure 6:
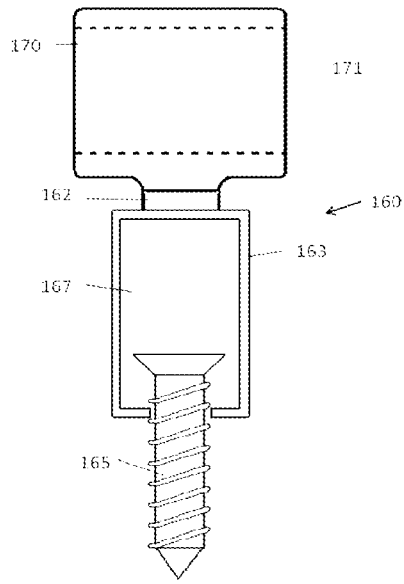
FIGS. 6-7 are front and side views of an alternative embodiment of the anchor element shown for use in conjunction with the spinous process fixation system of FIG. 1.
Figure 7:
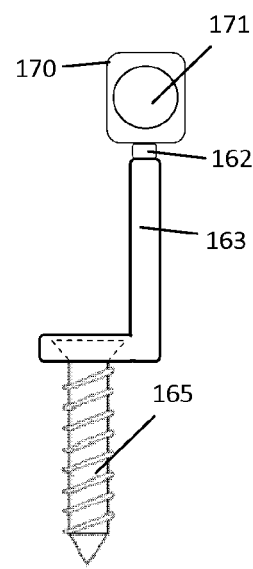

The anchor element 160 may have a number of end pieces in lieu of the coupling hook 166. For example, FIGS. 6-7 illustrate an alternative embodiment of the coupling hook 166 with the same function. According to this embodiment, the anchor element 160 is coupled to the connector element 16 of the spinous process fixation system 10 via a coupling sleeve 170 having a sleeve aperture 171 through which the connector element 16 passes. The connector element 16 is inserted though the coupling sleeve 170 prior to attachment of the connector element 16 to the first and/or second plates 12,14 and prior to insertion of the spinous process fixation system 10 into the patient. The anchor element 160 works in substantially the same way whether the coupling hook 166 or coupling sleeve 170 embodiment is utilized.

The anchor element 160 may be constructed from any of a variety of suitable materials without departing from the scope of the invention, including but not limited to titanium, polymeric materials (e.g. plastics) carbon fiber, and/or any other biologically acceptable material. The anchor element 160 may also be provided having any number of suitable dimensions without departing from the scope of the invention. For example, according to one embodiment, the width of the anchor element 160 may range from 3 mm to 30 mm, the length of the anchor element without the sacrum screw 165 may range from 10 mm to 40 mm, and the length of the sacrum screw 165 may range from 5 mm to 40 mm. It will be appreciated, however, that these dimensions are provided as examples of those that may be employed with the spinous process fixation system 10 of the present invention and any number of suitable modifications may be made depending upon a variety of factors without departing from the scope of the invention.

What is claimed is:

1. A spinous process fixation system for achieving fixation between a spinous process of an L5 vertebra to a sacrum, comprising:

a first plate including a first surface for contacting a first side of said spinous process and said sacrum, a second surface opposite said first surface, a first end portion, a second end portion, a generally elongated body portion having a first central aperture extending between said first and second portions and a first fin extending laterally from said second end portion;
a second plate including a first surface for contacting a second side of said spinous process and said sacrum, a second surface opposite said first surface, a first end portion, a second end portion, a generally elongated body portion having a second central aperture extending between said first and second end portions, and a second fin extending laterally from said second end portion;
a connector element extending through said first and second central apertures, said connector element reversibly coupled to at least one of said first and second plates; and
an anchor element dimensioned to span from the connector element into the sacrum and having a first end portion coupled to said connector element and a second end portion configured to be inserted into the sacrum.

2. The spinous process fixation system of claim 1, wherein the connector element has an anchor aperture.

3. The spinous process fixation system of claim 2, wherein the anchor element is coupled to the connector element via insertion through the anchor aperture.

4. The spinous process fixation system of claim 3, wherein the anchor element is a screw.

5. The spinous process fixation system of claim 1, wherein the anchor element further comprises a body between said first end portion and said second end portion.

6. The spinous process fixation system of claim 5, wherein said body of said anchor element includes a screw aperture for receiving a sacrum screw therethrough.

7. The spinous process fixation system of claim 6, wherein said second end portion comprises a sacrum screw.

8. The spinous process fixation system of claim 7, wherein said first end portion comprises a hook.

9. The spinous process fixation system of claim 7, wherein said first end portion comprises a sleeve.

10. The spinous process fixation system of claim 5, wherein said body of said anchor element is rotatable relative to said first end portion.

11. The spinous process fixation system of claim 1, wherein said first surfaces of said first and second plate include spikes.

* * * * *